United States Patent
Kortenbach et al.

(10) Patent No.: US 6,569,085 B2
(45) Date of Patent: May 27, 2003

(54) METHODS AND APPARATUS FOR DELIVERING A MEDICAL INSTRUMENT OVER AN ENDOSCOPE WHILE THE ENDOSCOPE IS IN A BODY LUMEN

(75) Inventors: Juergen A. Kortenbach, Miami Springs, FL (US); Charles R. Slater, Fort Lauderdale, FL (US); Michael Sean McBrayer, Miami, FL (US)

(73) Assignee: Syntheon, LLC, Miami, FL (US)

( * ) Notice: Subject to any disclaimer, the term of this patent is extended or adjusted under 35 U.S.C. 154(b) by 0 days.

(21) Appl. No.: 09/931,528

(22) Filed: Aug. 16, 2001

(65) Prior Publication Data

US 2003/0036679 A1 Feb. 20, 2003

(51) Int. Cl.[7] .................................................. A61B 1/00
(52) U.S. Cl. ........................ 600/104; 600/121; 600/124
(58) Field of Search .............................. 600/104, 121, 600/128, 123, 124, 125; 606/205, 207

(56) References Cited

U.S. PATENT DOCUMENTS

| | | | |
|---|---|---|---|
| 4,646,722 A | 3/1987 | Silverstein | 128/4 |
| 4,721,097 A | 1/1988 | D'Amelio | 128/4 |
| 4,741,326 A | 5/1988 | Sidall | 128/4 |
| 4,809,678 A | 3/1989 | Klein | 128/4 |
| 4,852,551 A | 8/1989 | Opie | 128/4 |
| 4,869,238 A | 9/1989 | Opie | 128/6 |
| 5,201,908 A | 4/1993 | Jones | 128/4 |
| 5,217,001 A * | 6/1993 | Nakao et al. | 600/123 |
| 5,257,617 A * | 11/1993 | Takahashi | 600/123 |
| 5,259,366 A * | 11/1993 | Reydel et al. | 600/124 |
| 5,386,817 A | 2/1995 | Jones | 128/4 |
| 5,394,885 A * | 3/1995 | Francese | 606/207 |
| 5,503,616 A | 4/1996 | Jones | 128/4 |
| 5,643,175 A * | 7/1997 | Adair | 600/123 |
| 5,938,586 A * | 8/1999 | Wilk et al. | 600/121 |
| 6,010,515 A | 1/2000 | Swain | 600/148 |
| 6,019,720 A | 2/2000 | Bito | 600/123 |
| 6,022,313 A | 2/2000 | Ginn | 600/114 |
| 6,059,719 A | 5/2000 | Yamamoto | 600/127 |
| 6,071,233 A * | 6/2000 | Ishikawa et al. | 600/104 |
| 6,179,776 B1 | 1/2001 | Adams | 600/121 |

OTHER PUBLICATIONS

Internet article from the NY Times, Jun. 9, 2001 entitled "Patients of Brooklyn Clinic are sought after Outbreak of Hepatitis C", 3 pages.

ndo Surgical advertisement for the Plicator procedure, 1 page, 2001.

* cited by examiner

*Primary Examiner*—Linda C. M. Dvorak
*Assistant Examiner*—Jocelyn Ram
(74) *Attorney, Agent, or Firm*—Gordon & Jacobson, P.C.

(57) ABSTRACT

Methods and apparatus for delivering a medical instrument over the exterior of an endoscope while the endoscope is installed in the patient's body allow the use of instruments which are too large to fit through the lumena of an endoscope. Furthermore, the invention allows the elimination of working lumena in an endoscope thereby minimizing the likelihood of contamination.

16 Claims, 6 Drawing Sheets

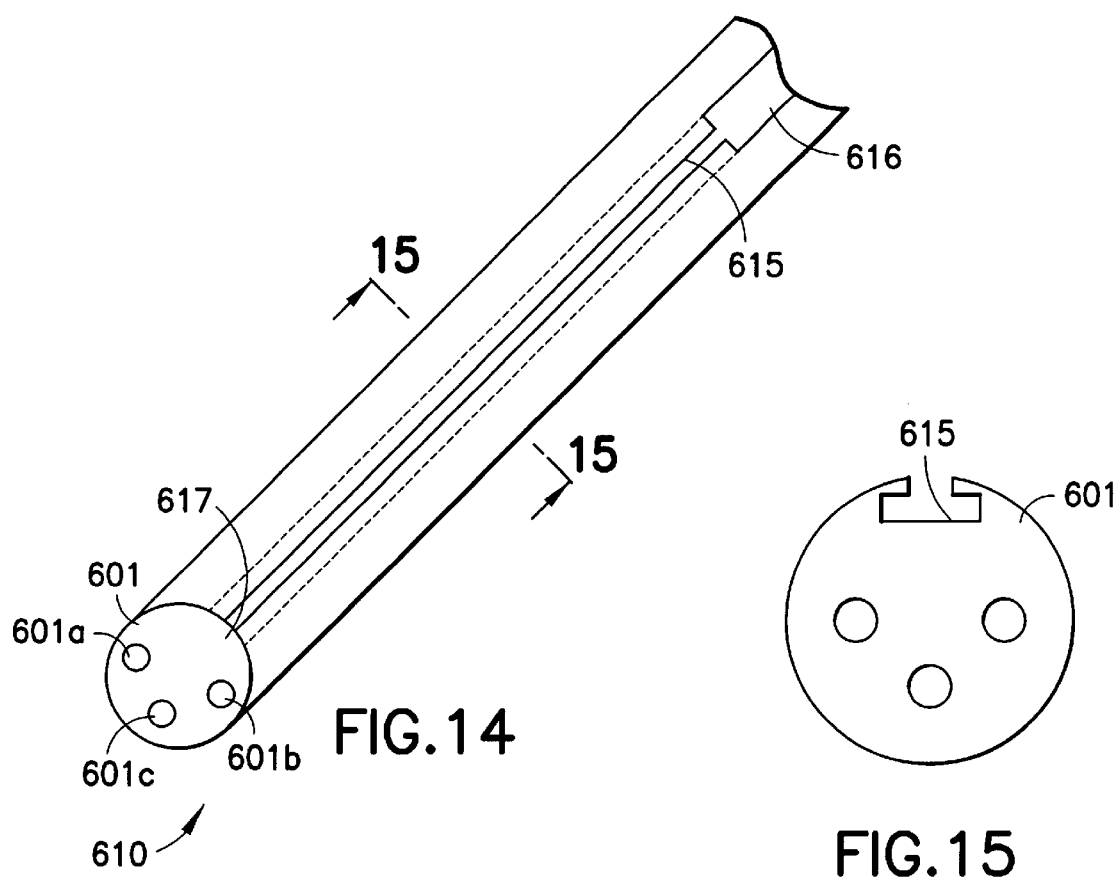
FIG. 14
FIG. 15
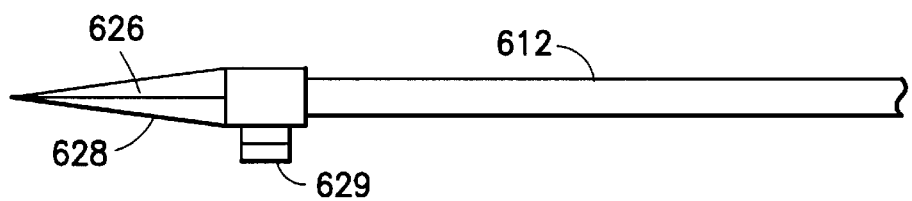
FIG. 16
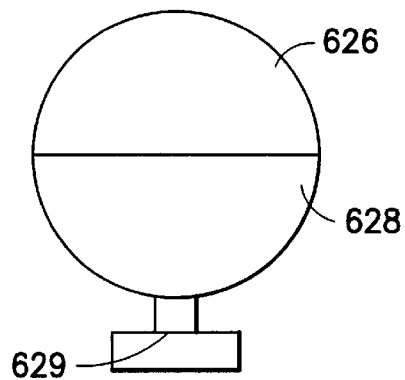
FIG. 17

METHODS AND APPARATUS FOR DELIVERING A MEDICAL INSTRUMENT OVER AN ENDOSCOPE WHILE THE ENDOSCOPE IS IN A BODY LUMEN

This application is related to co-owned, co-pending application Ser. No. 09/730,911 filed Dec. 5, 2000, the complete disclosure of which is hereby incorporated by reference herein.

BACKGROUND OF THE INVENTION

1. Field of the Invention

The invention relates to surgical instruments and methods. More particularly, the invention relates to methods and apparatus for the minimally invasive treatment of disease using an endoscope.

2. State of the Art

Minimally invasive (also known as endoscopic, laparoscopic, and arthroscopic) surgery is not a new technology. However, it is only in recent years that such surgery has become so widely accepted that it is used in many diverse procedures. Minimally invasive laparoscopic surgery typically involves the making of a small incision (5–10 mm) in the vicinity of the surgical site, the installation of a port through the incision, and the extension of a laparoscopic instrument through the port to the surgical site. Minimally invasive endoscopic surgery typically involves lubricating and inserting an endoscope through a body cavity such as the rectum or esophagus.

Gastrointestinal bleeding is a somewhat common and serious condition that can be fatal if left untreated. This problem has prompted the development of a number of endoscopic therapeutic approaches to achieve hemostasis, such as the injection of sclerosing agents, the attachment of mechanical hemostatic devices and contact electrocautery techniques. Mechanical hemostatic devices are typically in the form of clamps, clips, staples, sutures, etc. which are able to apply sufficient constrictive forces to blood vessels so as to limit or interrupt blood flow. Such devices are disclosed in U.S. Pat. No. 6,001,110. Electrocautery techniques involve the use of either monopolar or bipolar electrodes which are contacted to ulcerous tissue. A well known electrocautery device is disclosed in U.S. Pat. No. 5,336,222.

The known clip techniques and cautery techniques are only adequate for relatively small ulcers because the clips and/or cautery probes must be delivered through the working lumen of an endoscope. In particular, in addition to optical elements which carry fiber optics to illuminate the surgical site and which deliver an image from the surgical site, the endoscope typically has two or three lumena: one or two lumen (a) for aspiration and irrigation, and one (the working lumen) through which a surgical tool may be passed. The working lumen is typically very small in size (e.g., about 3 mm in diameter), and thus the size of the tools which may be used with a typical endoscope are severely limited in size. Bleeding ulcer lesions are typically 1.5 cm which is too large to be treated in one application with the known mechanicaal and electrical techniques.

Previously incorporated Ser. No. 09/730,911 discloses a medical instrument which fits over the distal end of an endoscope. As used herein, proximal end means the end closest to the practitioner and distal end means the end closest to the surgical site. The instrument includes a flexible coil having a proximal end and a distal end with a pull wire extending therethrough. An actuation device is coupled to the proximal ends of the coil and the pull wire for reciprocally moving one of the pull wire and the coil relative to the other. A pair of jaws are coupled to the distal ends of the coil and pull wire such that relative movement of the coil and pull wire causes opening and closing of the jaws. The jaws are rotatably coupled to a clevis which is adapted to be coupled to the distal end of an endoscope. At least one jaw has an "open" structure, with a rim but substantially no jaw cup. The jaws are U-shaped, semi-circular, or horse shoe shaped and are provided with a cautery capability by selectively coupling the coil, the pull wire, or both to a source of cauterizing energy. The clevis is attached to the distal end of an endoscope, prior to inserting the endoscope into the patient's body, and the distal end of the endoscope is delivered to the surgical site with the aid of the optics of the endoscope and with the jaws closed by activation of the actuation device.

Many procedures require the delivery of different surgical instruments via an endoscope during the course of the procedure. Typically, the surgical instruments are delivered through one of the lumena of the endoscope. As mentioned above, however, the lumena of the endoscope are relatively small and it is often desirable to have a larger instrument at the surgical site. The previously incorporated parent application teaches how to use a relatively large instrument in conjunction with an endoscope. However, the instrument must be attached to the endoscope before the endoscope is inserted into the patient's body.

Another issue has arisen with regard to endoscopes, particularly when an endoscope is inserted through the rectum or the esophagus, is the contamination of the endoscope and the resultant spread of disease from one patient to another. See, e.g., "Patients of Brooklyn Clinic Are Sought After Outbreak of Hepatitis C," New York Times Jun. 9, 2001, http://www.nytimes.com/2001/06/09/health/09HEPA.html?searchpv=day05. Because, the optical systems in most endoscopes are relatively sophisticated and expensive, it is prohibitively expensive to dispose of an endoscope after a single use. The endoscope, including the interior of its lumena must be carefully disinfected after each use. The dimensions of the lumena make them difficult to clean thoroughly. If they are not thoroughly cleaned, the next time a surgical instrument is passed through a lumen the instrument will become contaminated.

SUMMARY OF THE INVENTION

It is therefore an object of the invention to provide methods and apparatus for the minimally invasive treatment of disease using an endoscope.

It is also an object of the invention to provide methods and apparatus for the minimally invasive treatment of disease using an endoscope and a medical instrument larger than the working lumen of the endoscope.

It is another object of the invention to provide methods and apparatus for the minimally invasive treatment of disease using an endoscope and a medical instrument which is delivered over the endoscope after the endoscope has been inserted into the patient's body.

It is still another object of the invention to provide methods and apparatus for the minimally invasive treatment of disease using an endoscope wherein issues regarding contamination of the endoscope are minimized.

In accord with these objects which will be discussed in detail below, the present invention provides methods and apparatus for delivering a medical instrument over the exterior of an endoscope while the endoscope is installed in the patient's body. The invention allows the elimination or covering of the working lumena in an endoscope thereby minimizing the likelihood of contamination. Furthermore, the invention also allows the use of instruments which are too large to fit through the lumena of an endoscope.

A first embodiment of an apparatus of the invention includes a sheath or collar having a radial opening, so that it can be laterally attached to the exterior of an endoscope, and a surgical tool attached to the sheath or collar. The surgical tool is controlled by a flexible coil or tube having a proximal end and a distal end with a pull wire or other actuation means extending therethrough. An actuation device is coupled to the proximal ends of the coil and the pull wire for reciprocally moving one of the pull wire and the coil relative to the other. The distal ends of the coil and pull wire are coupled to the surgical tool such that manipulation of the actuation devices results in a manipulation of the surgical tool. A method for using the first embodiment includes slipping the collar over the endoscope via the radial opening and advancing the apparatus over the endoscope to the site of the procedure.

A second embodiment of an apparatus of the invention includes a medical instrument having a plurality of straps for attaching it to the exterior of an endoscope. A method for using the second embodiment includes attaching the straps over the endoscope and advancing the apparatus over the endoscope to the site of the procedure.

A third embodiment of an apparatus of the invention includes a medical instrument attached to the end of a flexible sheath having a reclosable seam. A method for using the third embodiment includes opening the seam, slipping the sheath over the endoscope, closing the seam, and advancing the apparatus over the endoscope to the site of the procedure.

A fourth embodiment of an apparatus of the invention includes a medical instrument attached to a bifurcated cylinder having a live hinge and a locking clip. The interior of the cylinder is preferably provided with a low friction surface. A method for using the fourth embodiment includes opening the cylinder, placing the cylinder halves adjacent the endoscope, closing the cylinder around the endoscope with the locking clip, and advancing the apparatus over the endoscope to the site of the procedure.

A fifth embodiment of an apparatus of the invention includes a flexible tube having a lumen and one or more tangential sheath(s) having a radial opening. A method for using the fifth embodiment includes attaching the flexible tube to the endoscope using the one or more tangential sheath(s) either before or after the endoscope is installed in the patient, and delivering a medical instrument through the lumen of the flexible tube to the site of the procedure. At the conclusion of the procedure, the apparatus is disposed as medical waste.

A sixth embodiment of an apparatus of the invention includes a flexible tube that can be loaded onto the endoscope before or after insertion into the patient. The flexible tube has a T-shaped track and a medical instrument having a T-shaped radial extension is designed to fit inside and ride along the T-shaped track. Alternatively, the T-shaped track can be built into the exterior surface of an endoscope. A method for using the fifth embodiment includes inserting the T-shaped radial extension of the medical instrument into the track and advancing the instrument to the site of the procedure.

Additional objects and advantages of the invention will become apparent to those skilled in the art upon reference to the detailed description taken in conjunction with the provided figures.

BRIEF DESCRIPTION OF THE DRAWINGS

FIG. 14 is a broken perspective view of an endoscope incorporating the sixth embodiment of an apparatus of the invention;

FIG. 15 is a section taken along line 15—15 in FIG. 14;

FIG. 16 is a broken side elevation view of a medical instrument adapted for use with the sixth embodiment; and FIG. 17 is an enlarged end view of the instrument of FIG. 16.

DETAILED DESCRIPTION OF THE PREFERRED EMBODIMENTS

Figure 1:
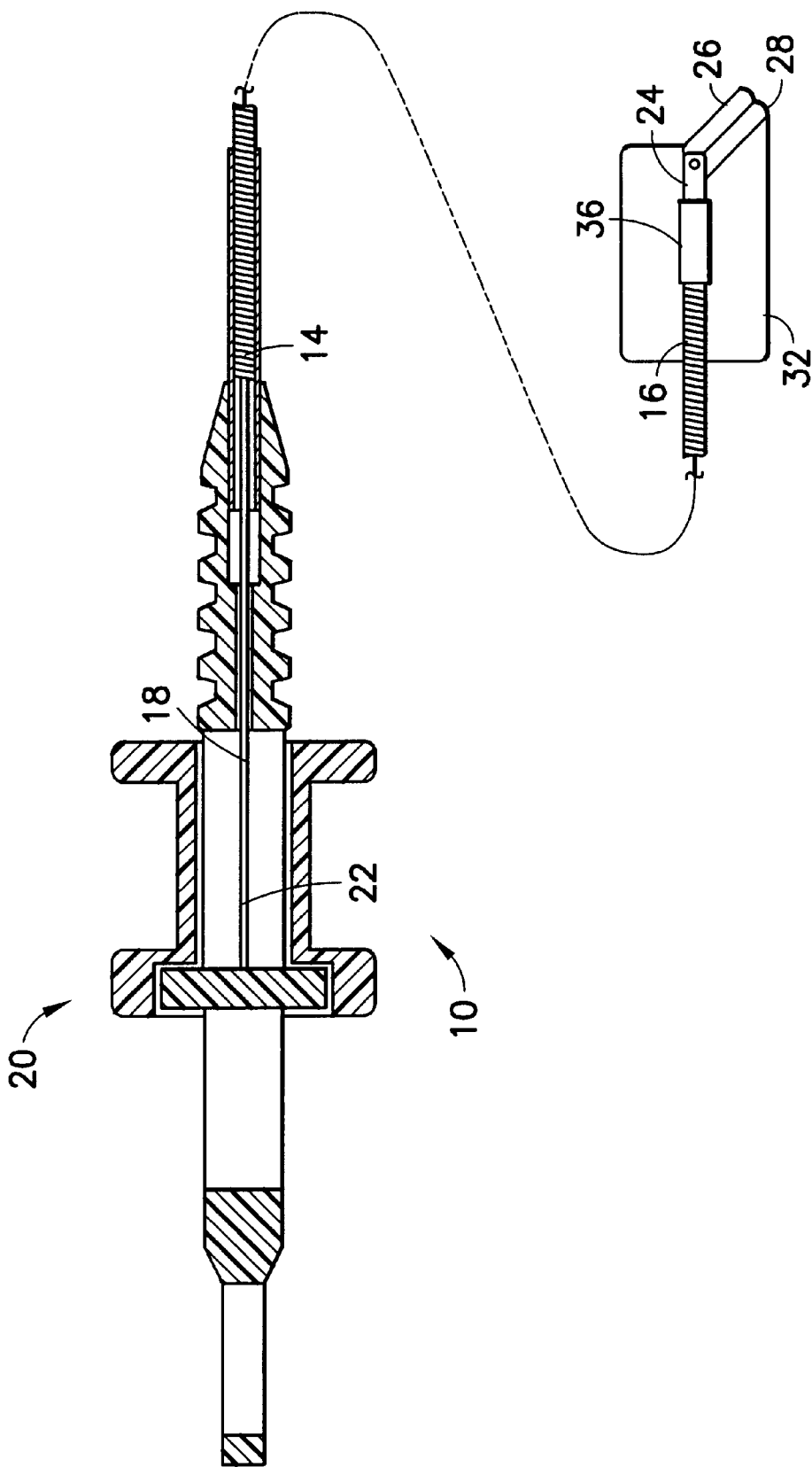
FIG. 1 is a broken side elevation view in partial section of a first embodiment of an apparatus of the invention.
Figure 3:
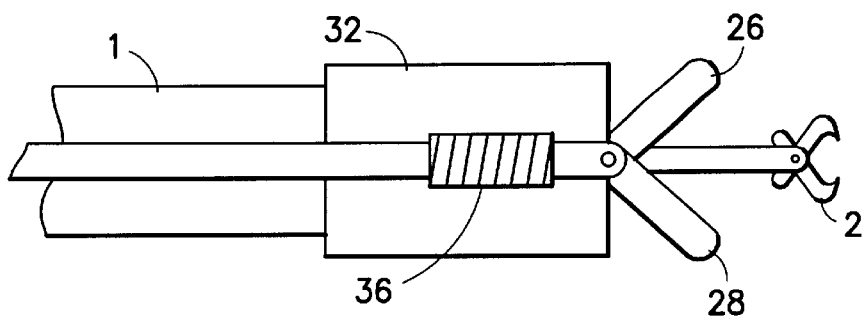
FIG. 3 is a broken side elevation view of the first embodiment attached to an endoscope.
Figure 2:
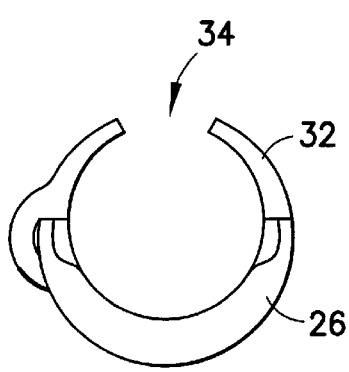
FIG. 2 is a distal end view of the first embodiment.

Referring now to FIGS. 1 through 3, an apparatus 10 according to a first embodiment of the invention includes a flexible coil 12 having a proximal end 14 and a distal end 16 with a pull wire 18 extending therethrough. An actuation device 20, described in more detail below, is coupled to the proximal end 14 of the coil and the proximal end 22 of the pull wire for reciprocally moving one of the pull wire and the coil relative to the other. A clevis 24 is coupled to the distal end 16 of the coil 12, and a pair of jaws 26, 28 are rotatably coupled to the clevis. The jaws 26, 28 are also coupled to the distal end (not shown) of the pull wire 18 such that movement of one of the pull wire or the coil relative to the other causes the jaws to open or close. According to the invention, the distal end 16 of the coil 12 is coupled to a collar 32 having a radial opening 34. The collar 32 is sufficiently resilient such that it can be snapped over an endoscope 1 (FIG. 3). The collar is preferably made of a polymer such as nylon, polycarbonate, ABS, etc.) and is sufficiently lubricous to slide over the outside of the endoscope 1. The jaws 26, 28 may be configured in different ways. However, it is preferable that the jaws be configured such that they can be moved to a position where they do not interfere with the optics of the endoscope 1 and such that they do not protrude significantly beyond the radius of the endoscope.

Figure 4:
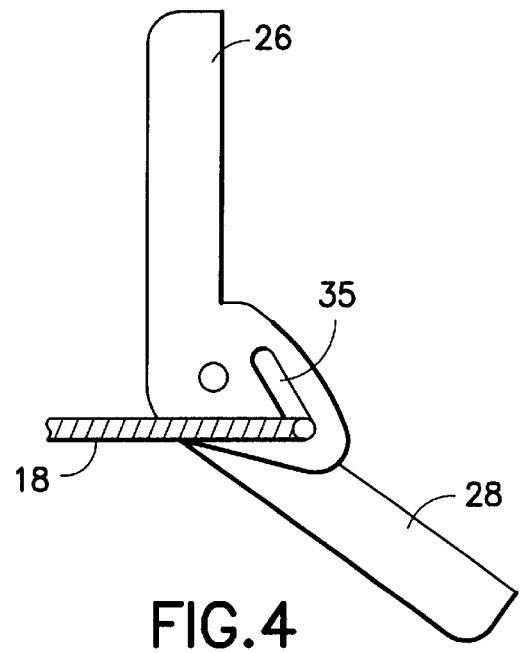
FIG. 4 is a broken side elevation view of the jaws of the first embodiment in the open position.
Figure 5:
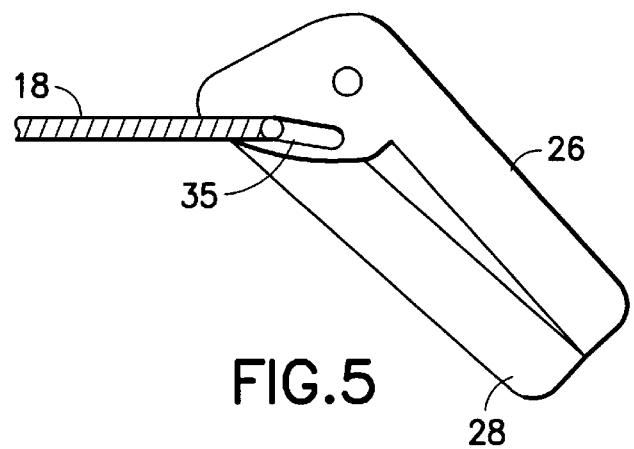
FIG. 5 is a broken side elevation view of the jaws of the first embodiment in the closed position.

The jaws 26, 28 in the first embodiment are configured as a hemostasis clip. According to this embodiment, the jaws are delivered to bleeding tissue near the end of the endoscope 1. Graspers 2 are delivered to the tissue through the working lumen of the endoscope 1. The graspers 2 are used to grasp the bleeding tissue (not shown) and pull the tissue in between the jaws 26, 28. The jaws 26, 28 are then closed over the tissue. According to this embodiment, the jaws are provided with a cam lock (35 in FIGS. 4 and 5) and a quick release 36 (FIG. 3). Referring now to FIGS. 4 and 5, the lower jaw 28 remains stationary and the upper jaw 26 is rotatable relative to the lower jaw. When the jaws are moved into the closed position shown in FIG. 5, the cam lock 35 locks the jaws in the closed position whereafter the jaws are separated from the apparatus 10 via the quick release 36. The apparatus 10 is then removed from the bleeding site and another pair of jaws are attached. The apparatus 10 with a new set of jaws is then delivered over the endoscope to a bleeding site for application of another clip. According to the presently preferred embodiment of the hemostasis clip, the jaws are provided with a force limiting feature, i.e. a thinned down portion of one of the jaws or wires which yields to the limit force. The quick release is preferably coupled to the cam lock in such a manner that the jaws cannot be released from the apparatus unless they are locked shut. This can be accomplished by a frangible link, e.g., between the pull wire 18 and the jaw 26. It is also preferable that the pull wire 18 be stiffer towards the proximal end. It will be appreciated that depending on the length of the collar 32, the jaws can be positioned some distance from the end of the endoscope 1.

Figure 6:
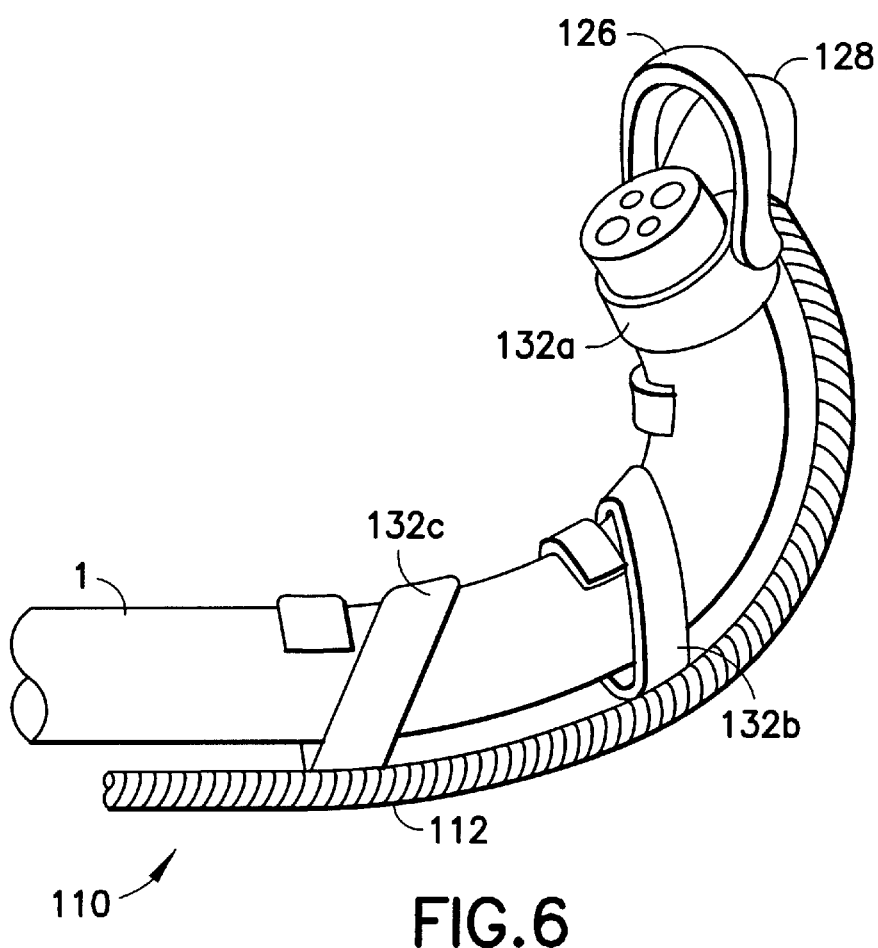
FIG. 6 is a broken perspective view of a second embodiment of an apparatus of the invention.

Turning now to FIG. 6, a second embodiment 110 is similar to the first embodiment with similar parts having similar reference numerals incremented by 100. According to this embodiment, a plurality of resilient straps 132a, 132b, 132c are arranged along the distal portion of the coil 112. The straps allow the instrument to be moved over the endoscope regardless of whether the endoscope is straight or curved. The method of using the second embodiment includes opening the straps, slipping the straps over the endoscope, allowing the straps to close, and moving the apparatus over the endoscope to the site of the procedure. Although the jaws 126, 128 appear to be the same as the jaws 26, 28, they need not be configured as a hemostatic clip which is discharged from the apparatus. They may be configured in a number of ways. For example, they may be configured as cautery jaws as described in the previously incorporated parent application. Another example is that they be configured as graspers to hold tissue which is being treated by a tool delivered through the working lumen of the endoscope.

Figure 7:
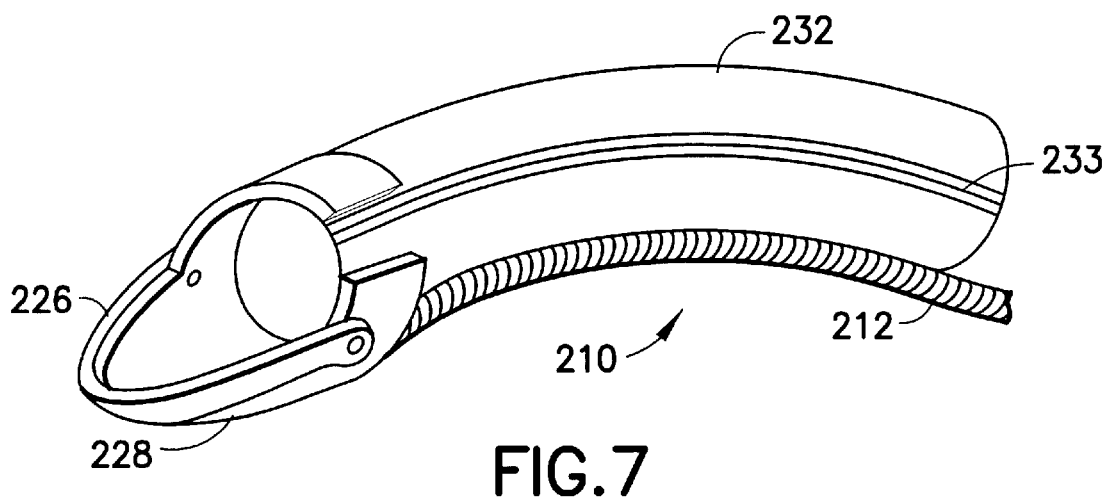
FIG. 7 is a broken perspective view of a third embodiment of an apparatus of the invention.
Figure 8:
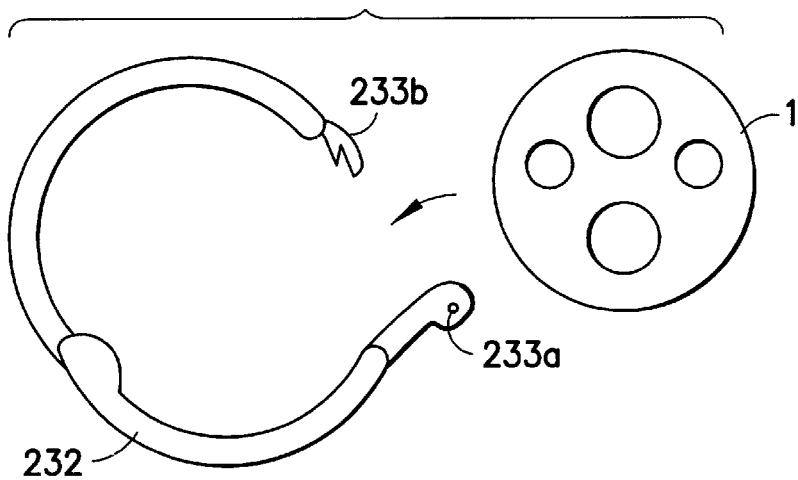
FIG. 8 is a distal end view of the third embodiment alongside an endoscope.
Figure 9:
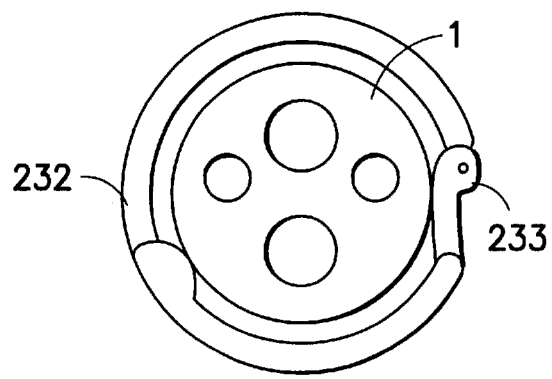
FIG. 9 is a distal end view of the third embodiment attached to an endoscope.

FIGS. 7 through 9 illustrate a third embodiment of the invention. The apparatus 210 is similar to the first embodiment with similar parts having similar reference numerals incremented by 200. The apparatus 210 includes a flexible control member 212 (e.g. a coil and pull wire) coupled to a pair of jaws 226, 228 which are mounted on the end of a flexible sheath 232 having a reclosable seam 233. The reclosable seam 233 can be configured in a number of ways. For example, the seam could be modeled after a ZIPLOC™ seam, a zipper, an adhesive tape, buttons, VELCRO™, etc. A method of using the apparatus 210 includes opening the seam to reveal two edges 233a, 233b as shown in FIG. 8, slipping the sheath over an endoscope 1, and reclosing the sheath as shown in FIG. 9. The length of the sheath is preferably long enough to offer stability but is much shorter than the endoscope. It will thus be appreciated that the sheath can be attached to the proximal end of an endoscope in situ and advanced over the endoscope to the site of the medical procedure.

Figure 10:
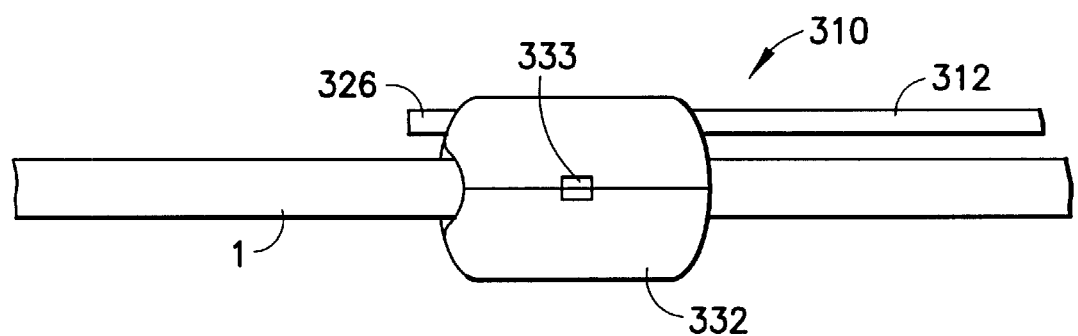
FIG. 10 is a broken side elevation view of a fourth embodiment of an apparatus of the invention attached to an endoscope.
Figure 11:
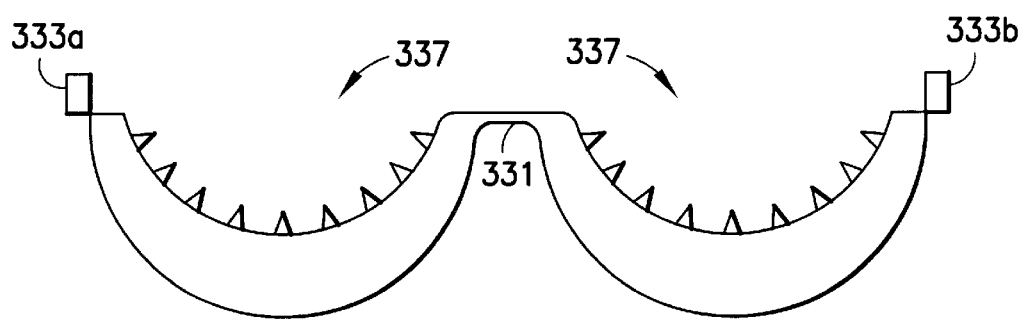
FIG. 11 is a side elevation view of the fourth embodiment opened and detached from the endoscope.

Turning now to FIGS. 10 and 11, a fourth embodiment 310 of the invention is similar to the first embodiment with similar parts having similar reference numerals incremented by 300. The apparatus 310 includes a bifurcated cylinder 332 having a live hinge 331 and a locking clip 333. A medical apparatus having a working end 326 and a control means 312 is fixedly attached to the cylinder. The interior of the cylinder is preferably provided with a low friction surface 337 such as soft pliable fingers or cilia as shown in FIG. 11 or a slippery coating. A method for using the apparatus 310 includes unlocking the locking clip 333 and folding the two cylinder halves at the live hinge 331 as shown in FIG. 11 thereby separating the ends 333a and 333b so that the cylinder may be placed over an endoscope. The cylinder is then closed about the endoscope 1 as shown in FIG. 10 and the locking clip 333 is locked. The cylinder 332 and the working end 326 of the medical apparatus are then slid along the endoscope to the site of the medical procedure.

Figure 12:
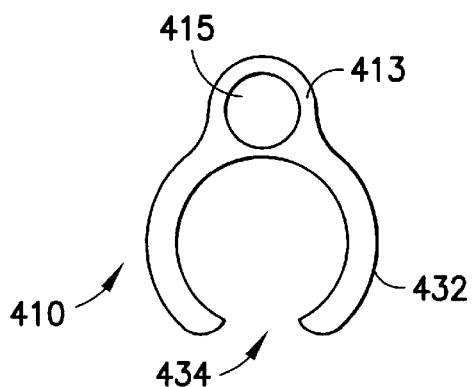
FIG. 12 is an end view of a fifth embodiment of an apparatus of the invention.
Figure 13:
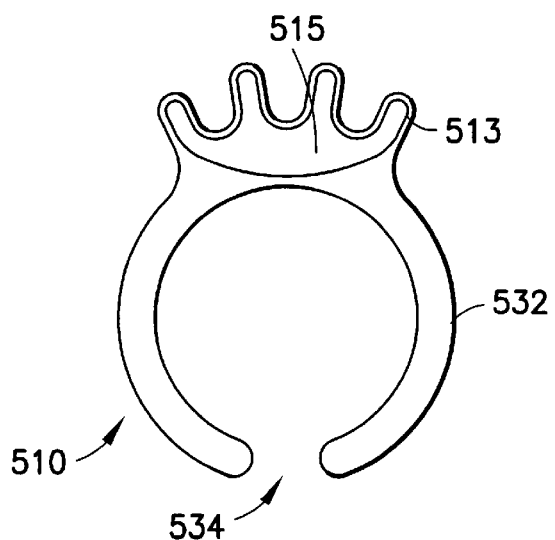
FIG. 13 is and end view of a variation of the fifth embodiment of an apparatus of the invention.

Fifth and sixth embodiments are illustrated in FIGS. 12 and 13 respectively. These two embodiment are very similar to each other but differ from the first four embodiments in several respects. Both apparatus 410 and 510 have a flexible polymer extrusion 432, 532 with a radial discontinuity 434, 534. Both apparatus have a tangential sheath 413, 513, defining a lumen 415, 515, permanently attached to the extrusion 432, 532. Like the first four embodiments, these two embodiments attach to an endoscope radially. Unlike the first four embodiments, however, the extrusions of these two embodiments are long enough to cover substantially the entire endoscope. The only difference between these two embodiments relative to each other is that the apparatus 410 has a relatively fixed tangential sheath 413 defining a lumen 415 having a substantially circular cross section. The apparatus 510 has a floppy tangential sheath 513 defining a lumen 515 having an irregular (collapsible) cross section. The methods of using these apparatus are substantially the same. Prior to introducing the endoscope into the body of the patient, the apparatus is attached to the endoscope by pressing the endoscope through the radial discontinuity until the extrusion envelops the endoscope along substantially all of its length. The endoscope is then delivered to the site of the procedure and the lumen 415, 515 are used to deliver instruments to the site. When the procedure is completed, the endoscope is removed from the patient and the apparatus 410, 510 is removed from the endoscope and discarded. The apparatus 410, 510 provide a disposable working lumen which need not be disinfected between procedures and also provide a prophylactic sheath which covers substantially all of the endoscope. The radial discontinuity 434, 534 makes it easy to attach the apparatus to an endoscope. It will be appreciated that a reclosable seam such as that described above with regard to the third embodiment may be advantageously applied to these two embodiments thereby further preventing contamination of the endoscope.

Turning now to FIGS. 14–17, the seventh embodiment of an apparatus 610 according to the invention includes an endoscope 601 having illuminating optics 601a, 601b, viewing optics 601c, and a tangential track 615 in lieu of a working lumen. As seen best in FIG. 15 the track 615 has an inverted T configuration. If desired, the track may be formed in an overtube (not shown) which is slid onto the endoscope before or after insertion into a patient. As shown in FIG. 14, a proximal portion 616 of the track 615 is widened such that the track has a substantially U shape in the widened region.

According to this embodiment, a medical tool having a pair of jaws 626, 628 and an actuation member 612 (e.g. a coil and pull wire) as shown in FIG. 16 is provided with a radially extending inverted T shaped track engaging member 629 as seen best in FIG. 17. Those skilled in the art will appreciate that the track engaging member 629 can be inserted into the proximal portion 616 of the track 615 and moved distally until the track is engaged. The jaws 626, 628 can then be advanced along the track to the side of a procedure. It will be appreciated that the distal end 617 of the track 615 shown in FIG. 14 is blocked so that the track engaging member 629 cannot be advanced off the track. The apparatus 610 allows the use of many different kinds of medical instruments so long as they are provided with a track engaging member.

There have been described and illustrated herein several embodiments of methods and apparatus for delivering a medical instrument over an endoscope while the endoscope is in a body lumen. While particular embodiments of the invention have been described, it is not intended that the invention be limited thereto, as it is intended that the invention be as broad in scope as the art will allow and that the specification be read likewise. Thus while the collars and sheaths which slide over the endoscope were described as being made from a polymer, other resilient materials could be used. Also, while particular grasping end effectors were shown, other types of instruments such as scissors, dissectors, staplers, suction/irrigation tubes, etc. could be used. It will therefore be appreciated by those skilled in the art that yet other modifications could be made to the provided invention without deviating from its spirit and scope as so claimed.

What is claimed is:

1. An apparatus for delivering a medical instrument over an endoscope to a procedural site while the endoscope is in a body lumen, said apparatus comprising:
   a) a collar dimensioned to fit over the endoscope and having a radial opening such that said collar may be fit over the endoscope radially;
   b) a medical instrument coupled to said collar; and
   c) actuation means coupled to said medical instrument for remotely operating said medical instrument, wherein said medical instrument includes a pair of opposed jaws.

2. An apparatus according to claim 1, wherein:
   said actuation means includes a flexible coil and a pull wire coupled to said jaws and a manually operable actuator coupled to said coil and pull wire.

3. An apparatus according to claim 2, wherein:
   said jaws have a locking cam such that they can be locked in the closed position, and
   said jaws are separable from said coil and pull wire.

4. An apparatus according to claim 1, wherein:
   said collar includes a plurality of spaced apart resilient straps.

5. An apparatus according to claim 1, wherein:
   said collar is a flexible sheath and said radial opening is a reclosable seam.

6. An apparatus according to claim 5, wherein:
   said reclosable seam is selected from the group consisting of a zipper, a ZIPLOC™, VELCRO™, an adhesive tape, snaps, and buttons.

7. An apparatus according to claim 1, wherein:
   said collar is a bifurcated cylinder having a live hinge and a locking clip.

8. An apparatus according to claim 7, wherein:
   said collar has an interior low friction surface.

9. An apparatus according to claim 8, wherein:
   said low friction surface is a slippery coating.

10. An apparatus according to claim 8, wherein:
    said low friction surface includes a plurality of cilia.

11. A method for delivering a medical instrument, the medical instrument including a pair of opposed jaws, over an endoscope to a procedural site while the endoscope is in a body lumen; said method comprising:
    a) attaching a medical instrument to a collar dimensioned to fit over the endoscope and having a radial opening such that said collar may be fit over the endoscope radially;
    b) attaching the collar to the endoscope by moving it radially over the endoscope;
    c) advancing the collar with the medical instrument along the surface of the endoscope to the procedural site; and
    d) opening and/or closing the jaws at the procedural site.

12. A method according to claim 11, wherein the endoscope has a working lumen, said method further comprising:
    e) closing the jaws onto a tissue;
    f) delivering a treating instrument through the working lumen of the endoscope to the tissue; and
    g) treating the tissue with the treating instrument while the tissue is grasped by the jaws of the medical instrument.

13. A method according to claim 11, further comprising:
    e) closing the jaws onto a tissue;
    f) locking the jaws closed; and
    g) detaching the jaws from the medical instrument.

14. A method according to claim 11, wherein:
    said collar includes a plurality of spaced apart resilient straps, and
    said step of attaching the collar to the endoscope includes placing the collar with its straps open adjacent the endoscope and closing the straps over the endoscope.

15. A method according to claim 11, wherein:
    said collar is a flexible sheath,
    said radial opening is a reclosable seam, and
    said step of attaching the collar to the endoscope includes placing the endoscope into the open seam and closing the reclosable seam.

16. A method according to claim 11, wherein:
    said collar is a bifurcated cylinder having a living hinge and a locking clip, and
    said step of attaching the collar to the endoscope includes closing the cylinder over the endoscope and locking it with the locking clip.

* * * * *